United States Patent [19]

Babb et al.

[11] Patent Number: 4,670,385

[45] Date of Patent: Jun. 2, 1987

[54] COMPOSITIONS AND ELEMENTS CONTAINING TRIARYLMETHANE LEUCO DYES AND METHODS USING SAME

[75] Inventors: Bruce E. Babb; Daniel S. Daniel, both of Rochester, N.Y.

[73] Assignee: Eastman Kodak Company, Rochester, N.Y.

[21] Appl. No.: 612,509

[22] Filed: May 21, 1984

[51] Int. Cl.$^4$ .................. C12Q 1/28; G01N 33/50
[52] U.S. Cl. ........................ 435/28; 422/56; 422/57; 422/60; 435/805; 436/135; 436/169; 436/170
[58] Field of Search .................. 435/28, 805; 436/135, 436/63, 169, 170; 422/57, 50, 56, 60

[56] References Cited

U.S. PATENT DOCUMENTS

| | | | |
|---|---|---|---|
| 2,981,606 | 4/1961 | Keston | 435/25 |
| 3,995,008 | 11/1976 | Garner et al. | 428/323 |
| 4,089,747 | 5/1978 | Bruschi | 195/99 |
| 4,273,868 | 6/1981 | Walter | 435/28 |
| 4,292,272 | 9/1981 | Kitajima et al. | 422/57 |
| 4,398,753 | 8/1983 | Asano et al. | 282/27.5 |
| 4,407,960 | 10/1983 | Tratnyek | 422/57 |

FOREIGN PATENT DOCUMENTS 53-074530 7/1978 Japan .
155433 10/1979 United Kingdom .

OTHER PUBLICATIONS

Draper et al, *J. Chromat.*, 216 (1981), pp. 413–416.
Mottola et al, *Anal. Chem.*, 42(3), pp. 410–411 (1970).

*Primary Examiner*—Sidney Marantz
*Assistant Examiner*—David A. Saunders
*Attorney, Agent, or Firm*—J. Lanny Tucker

[57] ABSTRACT

A particular class of triarylmethane leuco dyes are useful in analytical compositions, elements and methods. These leuco dyes are triarylmethane compounds having an aromatic heterocyclic moiety attached to the central methane carbon and which, upon interaction with hydrogen peroxide, provide dyes having a maximum absorption at a wavelength equal to or greater than about 600 nm. Particularly useful leuco dyes have the structure:

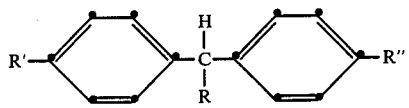

wherein R is a 5- to 15-membered aromatic heterocyclic moiety; and R' and R" are independently open chain or cyclic amines. These compounds are useful for providing detectable dyes in compositions and elements useful for detection of hydrogen peroxide or other analytes which react to produce hydrogen peroxide in aqueous liquids, e.g. biological fluids.

25 Claims, No Drawings

COMPOSITIONS AND ELEMENTS CONTAINING TRIARYLMETHANE LEUCO DYES AND METHODS USING SAME

FIELD OF THE INVENTION

This invention relates to a novel composition, element and method using particular leuco dyes to detect hydrogen peroxide or another analyte which reacts to produce hydrogen peroxide in the analysis of aqueous liquids, e.g. biological fluids. This invention is particularly useful in clinical chemistry.

BACKGROUND OF THE INVENTION

The detection and quantitative determination of hydrogen peroxide and compounds yielding hydrogen peroxide as a result of chemical or enzymatic reactions are of importance in many areas. For example, they are important in the detection of hydrogen peroxide produced in the enzymatic assay of chemical or biological substances (sometimes called analytes) such as glucose, cholesterol, uric acid, triglycerides, creatine kinase, etc. in the presence of oxygen. The quantity of analyte present in a specimen sample is determinable from the amount of hydrogen peroxide produced and detected.

Known compositions for detecting or quantifying hydrogen peroxide in such assays generally comprise a substance having peroxidative activity, e.g. peroxidase, and a material which undergoes a detectable change (e.g. a color change) in the presence of hydrogen peroxide and the peroxidative substance. Various materials which undergo such a detectable change include monoamines, diamines, phenols, leuco dyes and other known dyes or dye formers. Dye-providing materials also useful in such assays include triarylimidazoles as described, for example, in U.S. Pat. No. 4,089,747 (issued May 16, 1978 to Bruschi).

Triarylmethane dyes and their leuco precursors are also known as commercially useful compounds. Triarylmethane leuco dyes, for example, are known as useful indicators of hydrogen peroxide. Examples of such leuco dyes include the following compounds:

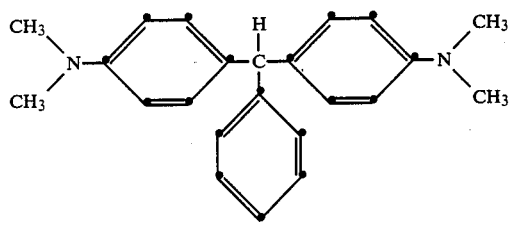

Leuco malachite green;

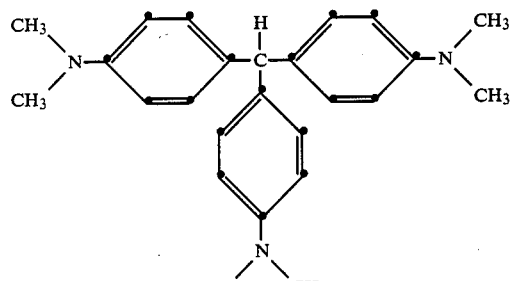

Leuco crystal violet;

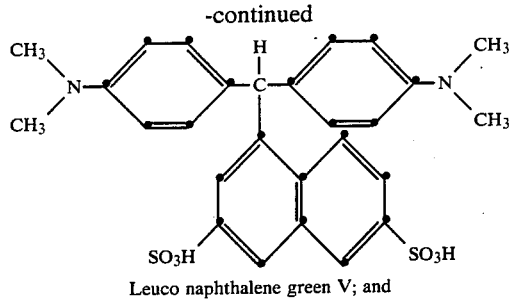

Leuco naphthalene green V; and

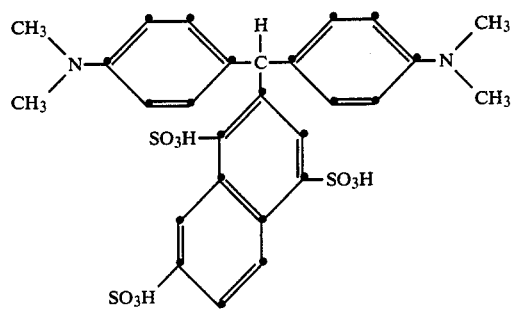

Leuco form of Acid Dye #3040.

However, it has been observed that such leuco dyes readily oxidize in air or in aqueous solutions containing a substance having peroxidative activity (see e.g. Example 1 hereinbelow). Hence, this instability renders them unsuitable for analytical determinations, and especially for dry assays where the analytical composition is stored for a period of time prior to use.

Although other dye-providing materials have the desired stability and are, in general, useful as indicators for hydrogen peroxide determination, there are instances when the concentration of hydrogen peroxide to be analyzed is too low to produce sufficient detectable color from such indicators. In some instances, this shortcoming can be overcome by using increased amounts of indicator. However, where the analyte concentration is initially low or high dilution of the test sample is required, such indicators may still be deficient because they still provide insufficient detectable color in such instances.

Such problems of instability and low analyte concentration are particularly acute when analyte determination is attempted with a dry analytical element, e.g. with the commercially successful elements described in U.S. Pat. No. 3,992,158 (issued Nov. 16, 1976 to Przybylowicz et al). In such instances, the indicator or reagent layer present in such elements is necessarily very thin, and the dye concentration is relatively low. Hence, the density of the color formed can be rather low even with high analyte concentrations. However, it would be desirable to use such elements for very low analyte concentrations.

Hence, there is a continuing need in the art for dye-providing materials which are stable to oxidation and which can be used to detect low concentrations of hydrogen peroxide or of analytes which react to produce same.

SUMMARY OF THE INVENTION

The present invention utilizes a particular class of leuco dyes which are unexpectedly stable to oxidation in air and in the presence of a peroxidative substance, but which can be advantageously used to detect low levels of hydrogen peroxide or analytes which react to produce hydrogen peroxide in both solution and dry assays. Advantageously, dyes obtained from these compounds have a maximum absorption at or above 600 nm thereby avoiding potential spectral interferents commonly found in biological fluids. These compounds are particularly useful for the determination of hydrogen peroxide generated by one or more (i.e. coupled or uncoupled) enzymatic reactions in response to an analyte such as glucose, galactose, amino acids, uric acid, triglycerides, creatine kinase, cholesterol and the like.

The leuco dyes useful in the practice of this invention are triarylmethane leuco dyes having an aromatic heterocyclic moiety attached to the central methane carbon atom.

Therefore, in accordance with this invention, a composition for determination of hydrogen peroxide in an aqueous liquid comprises a substance having peroxidative activity, and a triarylmethane leuco dye having an aromatic heterocyclic moiety attached to the central methane carbon atom which provides a dye having a maximum absorption at a wavelength equal to or greater than about 600 nm upon interaction with hydrogen peroxide. Such a composition is particularly useful for the determination of an analyte which reacts to provide hydrogen peroxide, and can include an interactive composition which produces hydrogen peroxide upon interaction with the analyte.

Still another feature of this invention is a dry analytical element for determination of hydrogen peroxide or an analyte which reacts to produce hydrogen peroxide. Such an element comprises a composition described in the preceding paragraph.

According to yet another feature of this invention, a method for determining hydrogen peroxide or an analyte which reacts to produce hydrogen peroxide in an aqueous liquid comprises the steps of: A. physically contacting a sample of the liquid with a composition comprising a substance having peroxidative activity and the leuco dye described hereinabove; and B. detecting the resulting dye at a wavelength equal to or greater than about 600 nm.

DETAILED DESCRIPTION OF THE INVENTION

The leuco dyes useful in the practice of this invention are triarylmethane compounds which have an aromatic heterocyclic moiety attached to the central methane carbon. These leuco dyes provide dyes, in the presence of hydrogen peroxide, which have a maximum absorption at a wavelength equal to or greater than about 600 nm. The leuco dyes also have two carbocyclic aryl groups attached to the central methane carbon. Generally, these carbocyclic aryl groups are the same although they can be different, if desired, and have from 6 to 14 carbon atoms (e.g. phenyl, naphthyl or anthryl). Preferably, each aryl group is phenyl. Further, each aryl group has an amino group (primary, secondary or tertiary) which is attached to the aryl ring in such a position as to allow dye formation, e.g. in the para position of a phenyl group. Preferably, the amino group is tertiary.

Particularly useful leuco dyes can be represented by the structure (I):

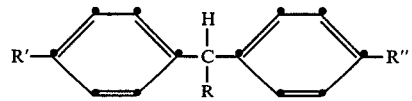

wherein R is a 5- to 15-membered aromatic heterocyclic moiety, and generally a mono- or poly-heterocyclic moiety containing carbon and one or more nitrogen, sulfur, oxygen or selenium atoms. Examples of R groups are illustrated hereinbelow. R' and R" are independently open chain (primary, secondary or tertiary) or cyclic amines. Preferably, R' and R" are independently tertiary open chain or cyclic amines. As used herein, a cyclic amine is represented by the structure

wherein Z represents the carbon, nitrogen, oxygen, sulfur or selenium atoms necessary to complete, with the illustrated nitrogen atom, a 5- to 15-membered mono-heterocyclic ring, as further identified hereinbelow for $R^1$, $R^2$, $R^3$, and $R^4$.

The leuco dyes preferred in the practice of this invention have the structure (II):

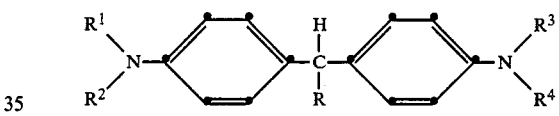

wherein R is a 5- to 15-membered aromatic heterocyclic moiety which can be unsubstituted or substituted with one or more substituents such as alkyl (preferably of 1 to 18 carbon atoms), aryl (preferably of 6 to 14 carbon atoms, e.g. phenyl, xylyl, etc.); alkoxy (preferably of 1 to 18 carbon atoms, e.g. methoxy, propoxy, n-pentoxy, etc.); halo (e.g. fluoro, chloro, bromo and iodo); nitro; cyano; amino as described hereinabove for R' and R"; carboxy; sulfo; carboxyesters; carbonylalkyl (preferably of 2 to 20 carbon atoms, substituted or unsubstituted); sulfones; sulfonamides; and the like. The heterocyclic moiety can be a mono- or polyheterocyclic ring and can contain carbon, nitrogen, sulfur, oxygen and selenium atoms in any combination. Examples of useful heterocyclic moieties include furyl, thienyl, selenophenyl, pyridyl, pyrindinyl, pyrimidyl, triazinyl, thiazolyl, oxazolyl, selenazolyl, pyranyl, pyrazinyl, quinolinyl, isoquinolinyl, tetrazinyl, pyridazinyl, quinazolinyl, acridinyl, benzothiazolyl, quinoxalinyl, cinnolinyl, phthalazinyl, pteridinyl, phenazinyl, N-methylpyrrole, N-methylindole, N-methylimidazole, N-methylbenzimidazole, etc. Heterocyclic moieties which are not useful are those containing an NH group in the ring, e.g. those derived from pyrrole, indole, imidazole, benzimidazole, etc. Preferred heterocyclic moieties are those which are π-deficient, including pyridyl, pyridazinyl, pyrimidyl, pyrazinyl, triazinyl, tetrazinyl, quinolinyl, isoquinolinyl, quinazolinyl, acridinyl, quinoxalinyl, cinnolinyl, phthalazinyl, pteridinyl, phenazinyl, pyrindinyl and the like. Particularly preferred R groups are 3-pyridyl and 4-pyridyl. For a definition of "π-deficiency", see the book by A. Albert, *Heterocyclic Chemistry*, 2nd Ed., Univ. of London, Athlone Press, Chapter 4 (particularly pp. 67-70), 1968.

In the above-identified structure, $R^1$, $R^2$, $R^3$ and $R^4$ are independently substituted or unsubstituted alkyl, preferably of 1 to 14 carbon atoms (e.g. methyl, chloromethyl, ethyl, n-propyl, isopropyl, hexyl, decyl, tetradecyl, etc.); substituted or unsubstituted alkaryl or aralkyl, preferably of 7 to 14 carbon atoms (e.g. benzyl, 2-ethylphenyl, p-methylbenzyl, methylnaphthyls, etc.); substituted or unsubstituted aryl, preferably of 6 to 14 carbon atoms in the aromatic nucleus (e.g. phenyl, p-nitrophenyl, xylyl, naphthyl, anthryl, etc.); or an aromatic or nonaromatic monoheterocyclic moiety, preferably of 5 to 15 atoms. Examples of aromatic heterocyclic moieties are given above in the definition of R. Examples of nonaromatic heterocyclic moieties include piperidinyl, pyrrolidinyl, morpholinyl and the like. Alternatively, $R^1$ and $R^2$ taken together, and $R^3$ and $R^4$ taken together can represent, with the nitrogen atom to which they are attached, the atoms needed to complete a substituted or unsubstituted heterocyclic ring, preferably of 5 to 15 atoms (i.e. carbon, oxygen, sulfur, nitrogen, selenium atoms), e.g. piperidinyl, morpholinyl, julolidinyl, piperazinyl and the like.

Preferably, $R^1$, $R^2$, $R^3$ and $R^4$ are independently substituted or unsubstituted lower alkyls of 1 to 6 carbon atoms (e.g. methyl, chloromethyl, ethyl, hexyl, etc.). More preferably $R^1$ is the same as $R^3$ and $R^2$ is the same as $R^4$. Most preferably, each of these groups is the same.

The arylene rings of the leuco dyes illustrated hereinabove can be further substituted, if desired, in the positions meta to the central methane carbon, with one or more (up to 2 each) lower alkyl (1 to 4 carbon atoms, substituted or unsubstituted), lower alkoxy (1 to 4 carbon atoms, substituted or unsubstituted, e.g. methoxy, ethoxy, etc.), halo (e.g. chloro, bromo, etc.), amino, or other groups known in the art. Electron donating groups, such as lower alkyl and lower alkoxy are preferred.

Upon oxidation by hydrogen peroxide and a substance having peroxidative activity (e.g. peroxidase), the leuco dyes are converted to detectable dyes which have a maximum absorption at or above 600 nm. This feature is advantageous in that dye detection is not hindered by certain spectral interferents (e.g. hemoglobin, bilirubin, etc.) commonly found in biological fluids. The following equation illustrates the conversion of leuco dye to positively-charged detectable dye:

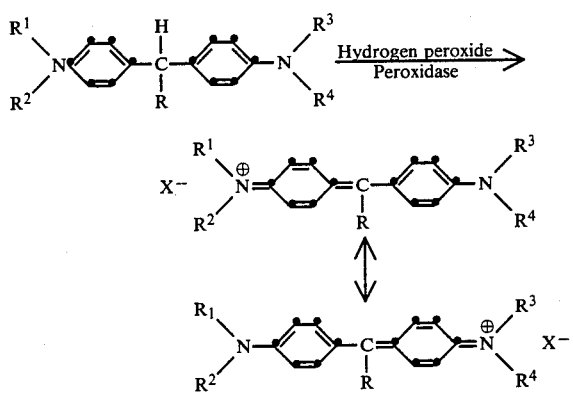

wherein $X^-$ is a suitable monovalent anion (e.g. halide, perchlorate, p-toluene sulfonate, etc.).

Representative leuco dyes are listed in Table I hereinbelow in reference to the compound structure (II) given hereinabove.

TABLE I

| Compound | R | $R^1$ | $R^2$ | $R^3$ | $R^4$ |
|---|---|---|---|---|---|
| I. | (pyridyl, N in ring) | —CH₃ | —CH₃ | —CH₃ | —CH₃ |
| II. | (pyridyl, N) | " | " | " | " |
| III. | (furyl, O) | " | " | " | " |
| IV. | (thienyl, S) | " | " | " | " |
| V. | (benzothiazolyl, N,S) | " | " | " | " |
| VI. | (methyl-thiazolyl, N,S—CH₃) | " | " | " | " |

TABLE I-continued

| Compound | R | R¹ | R² | R³ | R⁴ |
|---|---|---|---|---|---|
| VII. | (benzothiazole structure) | $-C_{10}H_{21}$ | " | $-C_{10}H_{21}$ | " |
| VIII. | (quinoline structure) | $-\underline{n}\text{-}C_3H_7$ | $-\underline{n}\text{-}C_3H_7$ | $-\underline{n}\text{-}C_3H_7$ | $-\underline{n}\text{-}C_3H_7$ |
| IX.* | (pyrrole structure) | taken together are —N⟩O | | taken together are —N⟩O | |
| X. | (methylthiazole structure) | $-C_2H_5$ | $-CH_2$-(phenyl) | $-C_2H_5$ | $-CH_2$-(phenyl) |
| XI. | (pyrimidine structure) | taken together are —N⟩ | | taken together are —N⟩ | |
| XII. | (triazine structure) | $-C_2H_5$ | $-C_2H_5$ | $-C_2H_5$ | $-C_2H_5$ |

*This leuco dye is also substituted with a methyl group on each phenylene ring in a position meta to the central methane carbon.

Leuco dyes I and II are preferred.

The leuco dyes useful in the practice of this invention can be readily prepared using commercially available or readily prepared starting materials. They can be prepared using synthetic procedures well known in the art as illustrated, for example, in U.S. Pat. No. 3,995,088 (issued Nov. 30, 1976 to Garner et al). In general, the leuco dyes of structure (II) are prepared by reacting a mole of an aldehyde of the formula RCHO with two moles of an amine or a mixture of amines (i.e. 2 moles of

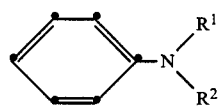

if R¹=R³ and R²=R⁴, or a 1:1 molar mixture of

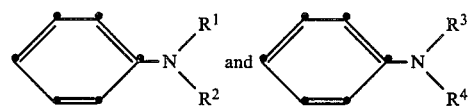

(if R¹, R², R³ and R⁴ are different) in the presence of a suitable catalyst (e.g. ZnCl₂).

The analytical composition of this invention can be used in both solution and dry element assays, and comprises a leuco dye as described hereinabove, a substance having peroxidative activity, and optionally but preferably, a buffer which maintains a pH of from about 4 to about 9 in the composition when it is used in either solution or dry assay.

Substances having peroxidative activity useful in the practice of this invention are also known as peroxidative substances and are capable of catalyzing the oxidation of another substance by means of hydrogen peroxide and other peroxides. Such substances include natural and synthetic peroxidases, cytochromes, hemin, forms of hemoglobin, alkaline hematin, iron sulfocyanate, iron tannate, chromic salts and the like. Peroxidase is a particularly useful peroxidative substance.

Substantially any buffer is useful in the composition of this invention. Useful buffers provide a pH in the composition which is conducive to dye formation. Generally, the pH is within the range of from about 4 to about 9, but a specific pH will depend to some extent on the particular analyte being assayed. For example, when used to detect uric acid using uricase, it is preferred to buffer the composition at a pH between about 8 and about 9. Useful buffers include carbonates, borates, phosphates, glutarates and the tris materials, e.g. tris(hydroxymethyl)aminomethane.

The compositions of this invention can be prepared for use in a solution assay by mixing the peroxidative substance (generally in an aqueous solution) with the leuco dye. Since the leuco dyes have limited solubility in water, they can be dissolved in a water-miscible solvent, such as an alcohol or N,N-dimethylformamide, prior to mixing with the peroxidative substance. The details of preparing a representative hydrogen peroxide determining composition are given in Example 2 hereinbelow.

When the compositions of this invention are used in solution assays, generally the leuco dye is present in a concentration of up to about 0.1, and preferably from about 0.02 to about 0.05, mg/mL of solution. Similarly, the peroxidative substance is present in an amount sufficient to catalyze the leuco dye-dye reaction. For example, peroxidase is present in an amount up to 1, and preferably from about 0.1 to about 0.5, U/mL. The amounts of the optional composition components (e.g. buffer, surfactant, etc.) and of the interactive composition (described hereinbelow) are within the skill of a worker in the art.

The compositions of this invention can be used to determine an analyte which is capable of producing hydrogen peroxide, i.e. it can participate in a reaction or series of reactions which produce hydrogen peroxide, in an aqueous liquid by including in such compositions an interactive composition which produces hydrogen peroxide upon interaction with the analyte. Analytes which can be determined in this manner include glucose, triglycerides, uric acid, cholesterol, galactose, amino acids, creatine kinase, and others known to one skilled in the clinical chemistry art. For example, an interactive composition for determining uric acid includes uricase, and an interactive composition for determining cholesterol includes cholesterol oxidase and cholesterol ester hydrolase. Further, an interactive composition for determining creatine kinase includes glycerol kinase, adenosine triphosphate and α-glycerophosphate oxidase. Other interactive compositions can be fashioned for a given analyte by those skilled in the art.

The compositions and method of this invention are adaptable to both solution and dry element assays. In a solution assay, generally the leuco dye, peroxidative substance and interactive composition, if included, are physically contacted and mixed with a liquid test sample in a suitable container (e.g. test tube, petric dish, beaker, cuvette, etc.). The resulting solution is incubated for a relatively short time (i.e. about 5 minutes) at a temperature of up to abour 25° C. The sample is then evaluated by measuring the amount of dye provided upon interaction with hydrogen peroxide. The amount of dye can then be correlated to the amount of hydrogen peroxide either initially present in the sample, or produced as a result of the presence of an analyte. Such an evaluation can be done visually or with suitable colorimetric detection equipment and procedures.

Alternatively, the composition and method of this invention can be utilized with a dry analytical element which can be a simple carrier matrix, i.e. thin sheet or self-supporting absorbent or bibulous material, such as filter paper or strips, which contain the leuco dye with or without the peroxidative substance. Preferably, such elements also contain the peroxidative substance. Such elements are known in the art as test strips, diagnostic elements, dip sticks, diagnostic agents and the like.

When employed in "dry chemistry" elements, the composition of this invention can be incorporated into a suitable carrier matrix by imbibition, impregnation, coating or another suitable technique. Useful carrier matrices are insoluble and maintain their structural integrity when exposed to water or physiological fluids such as urine or serum. Useful carrier matrices can be prepared from paper, porous particulate structures, cellulose, wood, glass fiber, woven and nonwoven fabrics (synthetic and nonsynthetic) and the like. A useful dry analytical element is made by imbibing a solution of the reagent composition into the matrix and drying. Useful materials and procedures for making such elements are well known in the art as exemplified in U.S. Pat. Nos. 3,092,465 (issued June 4, 1963 to Adams et al); 3,802,842 (issued Apr. 9, 1974 to Lange et al); 3,915,647 (issued Oct. 28, 1975 to Wright); 3,917,453 (issued Nov. 4, 1975 to Milligan et al); 3,936,357 (issued Feb. 3, 1976 to Milligan et al); 4,248,829 (issued Feb. 3, 1981 to Kitajima et al); 4,255,384 (issued Mar. 10, 1981 Kitajima et al); and 4,270,920 (issued June 2, 1981 to Kondo et al); and U.K. Pat. No. 2,052,057 (published Jan. 21, 1981).

Preferably, the dry analytical elements of this invention have at least one porous spreading zone. This zone can be a self-supporting carrier matrix (i.e. composed of a material rigid enough to maintain its integrity), but preferably it is carried on a separate supporting substrate (commonly called a support). Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al), the disclosure of which is incorporated herein by reference in its entirety. Alternatively, and preferably, the spreading zone is prepared from polymeric compositions (e.g. blush polymers) or particulate materials, with or without binding adhesives, as described in U.S. Pat. Nos. 3,992,158 (issued Nov. 16, 1976 to Przybylowicz et al) and 4,258,001 (issued Mar. 24, 1981 to Pierce et al), the disclosures of which are incorporated herein by reference in their entirety. Other useful spreading zone materials are described in W. German OLS No. 3,150,102 (published July 29, 1982) and Japanese Patent Publication No. 57(1982)-101760 (published June 24, 1982), both assigned to Konishiroku Photo. It is desirable that the spreading zone be isotropically porous, meaning that the porosity is the same in each direction in the zone as created by interconnected spaces or pores between particles, fibers, polymeric strands, etc.

Particularly useful spreading zones are those having a particulate structure formed by organo-polymeric particles and a polymeric adhesive for these particles as described in the Pierce et al patent noted hereinabove.

The elements can have more than one zone, e.g. one or more reagent zones, spreading zones, registration zone, mordant zone, radiation-blocking or filter zone, subbing zone, barrier zone, buffer zone, etc. The zones are generally in fluid contact with each other meaning that fluids, reagents and reaction products can pass between superposed regions of adjacent zones. Stated in another manner, fluid contact refers to the ability to transport components of a fluid between the zones in fluid contact. Preferably, the zones are separately coated layers, although two or more zones can be a single layer, or a zone can contain two or more separate layers. Besides the references noted hereinabove, suitable element formats and components are described, for example, in U.S. Pat. Nos. 4,042,335 (issued Aug. 16, 1977 to Clément); 4,132,528 (issued Jan. 2, 1979 to Eikenberry et al); and 4,144,306 (issued Mar. 13, 1979 to Figueras), the disclosures of which are incorporated herein by reference in their entirety.

The components of the compositions of this invention, i.e. peroxidative substance, leuco dye, interactive composition (if present), buffer (if present), etc. can be incorporated in any of the zones of the elements that would be suitable for the particular analysis. The location of individual components is within the skill of a worker in the clinical chemistry art.

In the elements of this invention, the amount of the leuco dye can be varied widely, but it is generally present in a coverage of up to about 5, and preferably from about 0.01 to about 2.5 g/m$^2$. The leuco dyes can be ball milled directly into the spreading or reagent layer material, or dissolved in a high boiling coupler solvent and dispersed in the layer. Useful coupler solvents include tri-m-cresyl phosphate and tri-o-tolyl phosphate. The peroxidative substance is present in a coverage within the skill of a worker in the art. For peroxidase, for example, the coverage is up to about 150,000, and preferably from about 50,000 to about 100,000 U/m$^2$. A variety of other desirable, but optional reagents and addenda can be present in the element in amounts known to one skilled in the art. Such materials include surfactants, buffers, binders, pigments, activators, reagents for the interactive compositions, etc.

One embodiment of this invention is a multilayer dry analytical element for determining an analyte. This element comprises a support having thereon, in order and in fluid contact, a hydrophilic layer containing a hydrophilic binder material (natural or synthetic), such as gelatin or polyacrylamide, and a spreading/reagent layer containing: (1) an interactive composition which produces hydrogen peroxide upon interaction with the analyte, (2) a substance having peroxidative activity, and (3) a leuco dye as described hereinabove.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, hydrogen peroxide or analyte determination is made by taking the element from a supply roll, chip packet or other source and physically contacting it with a sample of the liquid to be tested. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

Determination of hydrogen peroxide or an analyte is achieved when the leuco dye is oxidized to provide a detectable dye. This dye can be detected with the unaided eye or with suitable spectrophotometric means and procedures. Generally, the dyes formed in the practice of this invention have a $\lambda_{max}$, or an absorption maximum, equal to or greater than 600 nm.

The following preparations and examples are provided to illustrate the practice of the invention. In those examples; Estane TM was obtained from B. F. Goodrich (Cleveland, Ohio); Alkanol TM XC was obtained from E. I. duPont (Wilmington, Del.); Surfactant 10G TM was obtained from Olin Mathieson Co. (Stamford, Conn.); and Triton TM X-102, Triton TM X-100 and Triton TM X-200 were obtained from Rohm & Haas (Philadelphia, Pa.). Peroxidase was obtained from Miles Laboratories, Elkhart, Ind. Glycerol kinase was obtained from Beckman Clinical Diagnostics Division (Carlsbad, Calif.) All other reagents (including enzymes) were obtained from Aldrich Chemicals Co. (Milwaukee, Wis.), Sigma Chemical Co. (St. Louis, Mo.) or Eastman Kodak Company (Rochester, N.Y.).

Air stability of both the leuco dyes useful in the practice of this invention and those known in the art was demonstrated by allowing a sample of each leuco dye to be exposed to air for several weeks. Only slight oxidation, as evidenced by a slight color formation, was observed in the case of the leuco dyes useful in this invention. The leuco dyes tested in the following examples were stable in the analytical solutions and elements prepared until oxidized by hydrogen peroxide in the presence of peroxidase. Leuco dyes outside the scope of this invention, e.g. leuco malachite green and leuco crystal violet, were readily oxidized in air.

The maximum absorption of the dyes formed by the leuco dyes useful in this invention were measured in the following manner: a stock solution of 1–5 mg of the leuco dye in 100 mL of methanol was prepared. Ten mL of the stock solution was mixed with 0.1 mL of an aqueous solution of peroxidase (100 units per mL of water) and 0.1 mL of a 0.1 M hydrogen peroxide solution. The resulting solution was diluted to 50 mL with methanol and water, and after 2 hours, the resulting spectra were determined in a conventional Carey spectrophotometer.

Preparation of Leuco Dye I (Table I)

A mixture of 4-pyridinecarboxaldehyde (11 g), N,N-dimethylaniline (25 g) and anhydrous zinc chloride (5 g) was heated under a nitrogen atmosphere at 150° C. for two hours. The resulting hot melt was poured into water and the mixture was made strongly alkaline by the addition of dilute sodium hydroxide. This mixture was then steam distilled to remove excess dimethylaniline. After cooling, the water was decanted from the residue yielding a sticky solid. This solid was dissolved in ethanol and filtered to remove zinc oxide. The filtrate was cooled, diluted with water and allowed to stand until crystallization of the product was complete. The product was collected and recrystallized from acetonitrile to yield 10 g of leuco dye I. Mass spectral analysis showed a parent ion at m/e 331 and no recognizable impurities. The leuco dye was very stable in air and the maximum absorption of the corresponding dye was at 630 nm.

Preparation of Leuco Dye II (Table I)

This compound was prepared in a manner similar to the preparation of leuco dye I, but using 3-pyridinecarboxaldehyde. The resulting product had a m.p. of 187°–189° C. and mass spectral analysis showed a parent ion at m/e 331 and no recognizable impurities. The leuco dye was very stable in air and the corresponding dye had a maximum absorption at 632 nm.

Preparation of Leuco Dye III (Table I)

A mixture of 2-furaldehyde (10 g), N,N-dimethylaniline (30 g) and anhydrous zinc chloride (14 g) was heated together at 100° C. under a nitrogen atmosphere until essentially all of the aldehyde was consumed, as indicated on thin layer chromatography (silica, 4:1 toluene/ethyl acetate). The reaction time was about 2 hours. Dilute potassium hydroxide solution was then added, and the resulting solution was steam distilled to remove excess N,N-dimethylaniline. The residue was extracted with ethyl acetate, filtered and the organic layer separated. After drying over magnesium sulfate, the solvent was concentrated under reduced pressure. The residue crystallized on cooling, and was recrystallized from ethyl alcohol. The yield was 15 g and TLC analysis showed one major spot. Mass spectral analysis showed a parent ion at m/e 336 and no recognizable impurities. This leuco dye was very stable to air. The maximum absorption of the corresponding dye was at 628 nm.

Preparation of Leuco Dye V (Table I)

Acetone (58 g) was brominated according to the procedure described by C. Rappe in *Arkiv För Kemi*, 21(46), 512 (1963) to provide 153 g of Intermediate A,

This compound (145 g) was reacted with

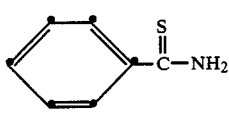

(69 g) according to the procedure described by Baganz and Rüger in *Chem. Ber.*, 101, pp. 3872–3882 (1968) to provide 203 g of Intermediate B

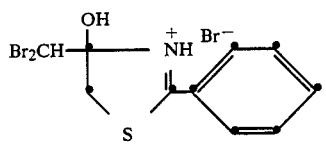

Intermediate B (44 g) was converted to 29 g of Intermediate C

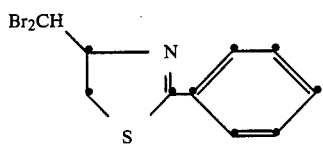

in the presence of sulfuric acid as described by Baganz et al, supra. Intermediate C (29 g) was then converted to 14 g of Intermediate D,

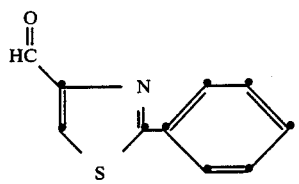

according to Baganz et al, supra. Thin layer chromatography (silica, 4:1 toluene/ethyl acetate) showed one product.

A mixture of Intermediate D (13 g), N,N-dimethylaniline (20 g) and anhydrous zinc chloride (10 g) was heated to 120° C. A vigorous reaction commenced and water was expelled from the mixture. After the reaction had subsided, the mixture was heated to 150° C. for a few minutes. The resulting viscous syrup was poured into a dilute potassium hydroxide solution with stirring. The resulting mixture was extracted with ethyl acetate, the solvent was dried and concentrated under reduced pressure. The residue solidified on addition of a small amount of ethyl alcohol. Recrystallization from acetonitrile gave 15 g of leuco dye V. TLC (silica, 4:1 toluene/ethyl acetate) showed one product. Mass spectral analysis showed one parent ion at m/e 413 and no recognizable impurities. The leuco dye was very stable to air. The maximum absorption of the corresponding dye was at 635 nm.

EXAMPLE 1

Comparison of Leuco Dyes

This is a comparison of the stability of a leuco dye useful in the practice of this invention to a known leuco dye, leuco naphthalene green V which has the structure:

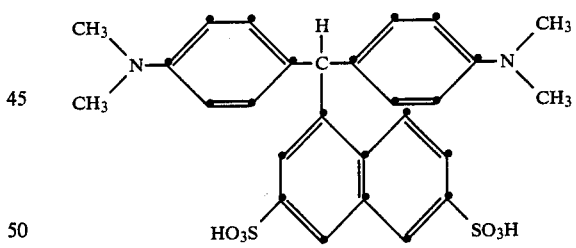

A test solution was prepared from 0.1 mL of a 5 mM solution of leuco naphthalene green V and 0.8 mL of 50 mM phosphate buffer (pH 7). Upon addition of 0.01 mL peroxidase (2 µg/mL), dye formation was observed within 5 minutes, indicating instability of the leuco dye in the presence of a peroxidative material. In contrast, leuco dye 11 which is useful in this invention, when treated in a similar manner, did not produce dye after one hour

EXAMPLE 2

Solution Assay of Hydrogen Peroxide

A leuco dye within the scope of this invention was used to determine hydrogen peroxide in solution in the following manner A 0.3 mL aliquot of a stock methanol solution of leuco dye 11 (about 5 mM) was diluted 10:1 with aqueous buffer solution (pH 7), then 0.1 mL of an aqueous peroxidase solution (100 units of peroxidase per mL of water), and 0.1 mL of a 0.1M hydrogen peroxide solution were added. Dye formation was observed after about 5 minutes with this composition. In contrast, no dye was observed after 60 minutes when the dye was mixed with only the buffer or peroxidase or both.

EXAMPLE 3

Solution Assay for Glucose

A leuco dye useful in this invention was used to assay for glucose in solution by the following procedure. Two stock solutions were prepared: stock solution A contained 50 mL of potassium phosphate buffer (pH 7) and 10 mL of a methanol solution of leuco dye II (21.9 mg of leuco dye/100 mL of methanol); stock solution B contained 5 mL of potassium phosphate buffer (pH 7), peroxidase (120 U/mL) and glucose oxidase (100 U/mL).

A control solution was prepared from 1 mL of solution A, 1 mL of solution B and 1.4 mL of distilled water. A test solution was prepared from 1 mL of solution A, 1 mL of solution B, 1 mL of distilled water and 0.4 mL of glucose solution (10 mM). The optical density of the control and test solutions were then measured at 25° C. at 632 nm in a conventional Carey spectrophotometer. The difference in density between the two solutions after one minute was 0.12 optical units indicating that the test solution of this invention was useful for determination of glucose.

EXAMPLE 4

Multilayer Elements Using Leuco Dyes I–VI for Determining Hydrogen Peroxide

Leuco dyes I–VI were used to determine hydrogen peroxide with individual multilayer analytical elements by incorporating each leuco dye into an individual element, contacting those elements with solutions containing hydrogen peroxide and measuring the reflection density of the resulting dye.

Each analytical element had the following format:

| Spreading/Reagent Layer | Barium sulfate | 5–50 g/m$^2$ |
|---|---|---|
| | Cellulose acetate | 0.4–4 g/m$^2$ |
| | Estane ™ elastomer | 0.05–1 g/m$^2$ |
| | Triton ™ X-102 surfactant | 0.06–0.25 g/m$^2$ |
| | Potassium phosphate buffer (pH 7) | 0.04–0.2 g/m$^2$ |
| | Sodium phosphate buffer (pH 7) | 0.02–0.1 g/m$^2$ |
| | Dimedone | 0.01–0.05 g/m$^2$ |
| | 4-Hydroxypyrimidine | 0.001–0.01 g/m$^2$ |
| | Leuco dye | 0.06–0.5 g/m$^2$ |
| | Peroxidase | 30,000–150,000 U/m$^2$ |
| Hydrophilic Layer | Gelatin | 5–20 g/m$^2$ |
| | Surfactant 10G ™ | 0.03–0.2 g/m$^2$ |
| | Poly(ethylene terephthalate) Support | |

The elements were evaluated using two hydrogen peroxide test solutions: test solution A (pH 5) contained $5 \times 10^{-2}$ $10^{-2}$M dimethylglutaric acid and $10^{-2}$M hydrogen peroxide; test solution B (pH 7) contained $5 \times 10^{-2}$M sodium dihydrogen phosphate, $5 \times 10^{-2}$M potassium hydrogen phosphate and 10 hydrogen peroxide. Water was used as a control liquid. Ten μL of each solution were spotted onto individual samples of the elements containing the respective leuco dyes. After 5 minutes incubation at 37° C., the reflection density was measured in a modified conventional reflectometer at 630 nm.

Table II hereinbelow shows the change in reflection density ($\Delta D_R$) between the water control and each test solution with each leuco dye. It is apparent from these data that each of the leuco dyes is effective in determining hydrogen peroxide at both pH 5 and pH 7 in a dry element.

TABLE II

| Leuco Dye | $\Delta D_R$ at 630 nm, Solution A | $\Delta D_R$ at 630 nm, Solution B |
|---|---|---|
| I | 0.89 | 1.1 |
| II | 0.41 | 1.0 |
| III | 0.25 | 0.29 |
| IV | 0.56 | 0.23 |
| V | 0.78 | 0.42 |
| VI | 0.86 | 0.37 |

EXAMPLE 5

Multilayer Element for Determination of Triglycerides

An analytical element was prepared as shown in the following format.

| Spreading Layer | Lipase M | 600–2400 U/m$^2$ |
|---|---|---|
| | Triton ™ X-100 | 2.7–11 g/m$^2$ |
| | Titanium dioxide | 25–200 g/m$^2$ |
| | Cellulose acetate | 3–30 g/m$^2$ |
| | Estane ™ polyurethane resin | 0.5–5 g/m$^2$ |
| Subbing Layer | Poly(N—isopropylacrylamide) | 0.1–1.0 g/m$^2$ |
| Hydrophilic Layer | Gelatin | 2–20 g/m$^2$ |
| | BVSME hardener | 0.02–0.08 g/m$^2$ |
| | Boric acid | 0.6–2.5 g/m$^2$ |
| | Triton ™ X-100 | 0.3–0.12 g/m$^2$ |
| | Ascorbic acid oxidase | 1000–5000 U/m$^2$ |
| Reagent Layer | Gelatin | 2–15 g/m$^2$ |
| | Poly(methylacrylate-co-2-acrylamido-2-methylpropane sulfonic acid-co-2-acetoacetoxymethacrylate) | 2–15 g/m$^2$ |
| | Leuco dye I | 0.2–2.5 g/m$^2$ |
| | Tricresyl phosphate | 1–7.5 g/m$^2$ |
| | Alkanol ™ XC | 0.1–0.4 g/m$^2$ |
| | Magnesium chloride | 0.1–0.4 g/m$^2$ |
| | Boric acid | 0.6–2.4 g/m$^2$ |
| | Adenosine triphosphate (ATP) | 0.6–2.4 g/m$^2$ |
| | Triton ™ X-200 | 0.02–0.1 g/m$^2$ |
| | Glycolic acid | 0.1–0.4 g/m$^2$ |
| | BVSME hardener | 0.02–0.08 g/m$^2$ |
| | Peroxidase | 7000–50,000 U/m$^2$ |
| | Glycerol kinase | 400–2000 U/m$^2$ |
| | Glycerophosphate oxidase | 1500–10,000 U/m$^2$ |
| | Poly(ethylene terephthalate) Support | |

To evaluate this coated element, a series of triglyceride calibrator fluids, varying in analyte concentration from 17.4 mg/mL to 565.8 mg/dL, were prepared, and samples of the element were spotted with 10 μL drops of each calibrator fluid. After 5 minutes incubation at 37° C., the reflection density ($D_R$) was measured at 650 nm in a modified conventional reflectometer. The results are listed in Table III hereinbelow. These data indicate that the element of this invention illustrated in this example is suitable for determining triglycerides.

TABLE III

| Calibrator Fluid-Triglyceride Concentration (mg/dL) | $D_R$ at 650 nm |
| --- | --- |
| 17.4 | 0.020 |
| 94.4 | 0.106 |
| 250.0 | 0.120 |
| 400.6 | 0.126 |
| 565.8 | 0.141 |

The invention has been described in detail with particular reference to preferred embodiments thereof, but it will be understood that variations and modifications can be effected within the spirit and scope of the invention.

We claim:

1. A composition for the determination of hydrogen peroxide in an aqueous liquid, said composition comprising a substance having peroxidative activity and a triarylmethane leuco dye which provides a dye having a maximum absorption at a wavelength equal to or greater than about 600 nm upon interaction with hydrogen peroxide, said leuco dye having the structure:

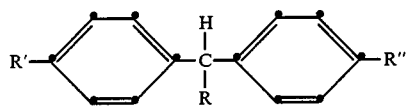

wherein R is a 5- to 15-membered aromatic heterocyclic moiety provided that said moiety does not have an —NH— group in the ring; and R' and R" are independently open chain or cyclic amines.

2. The composition of claim 1 wherein said substance having peroxidative activity is peroxidase.

3. The composition of claim 1 wherein said leuco dye has the structure:

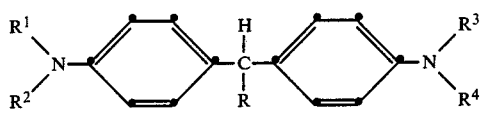

wherein $R^1$, $R^2$, $R^3$ and $R^4$ are independently alkyl, alkaryl, aralkyl, aryl or a heterocyclic moiety, or $R^1$ and $R^2$ or $R^3$ and $R^4$ independently taken together with the respective nitrogen atom, represent the atoms necessary to complet a heterocyclic ring, 4. The composition of claim 3 wherein each of $R^1$, $R^2$, $R^3$ and $R^4$ is a lower alkyl of 1 to 6 carbon atoms.

5. The composition of claim 3 wherein R is a $\pi$-deficient heterocycliic moiety.

6. The composition of claim 3 wherein $R^1 = R^3$ and $R^2 = R^4$.

7. The composition of claim 6 wherein $R^1$, $R^2$, $R^3$ and $R^4$ are the same.

8. The composition of claim 3 wherein said leuco dye is selected from the group consisting of:

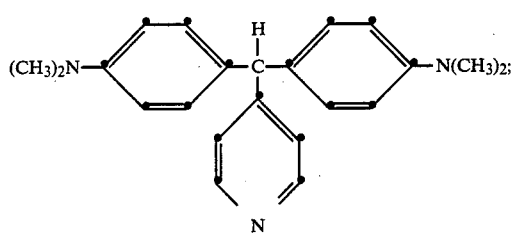

I.

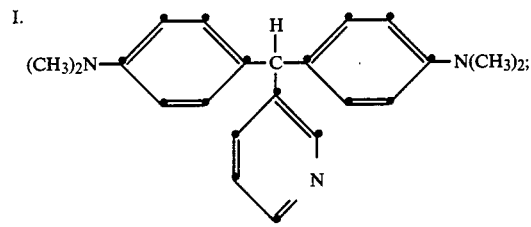

II.

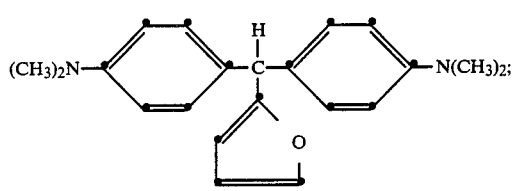

III.

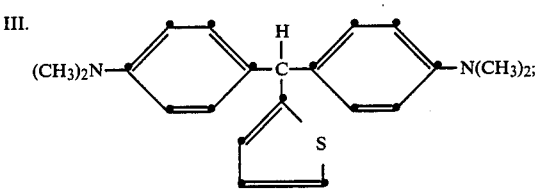

IV.

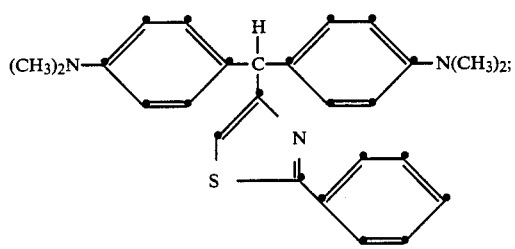

V.

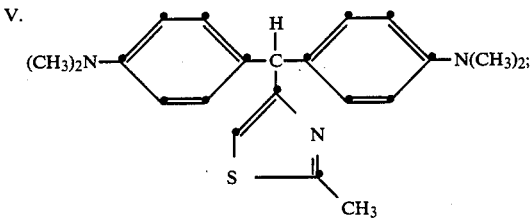

VI.

-continued

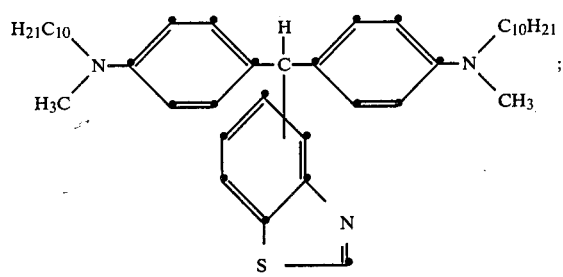

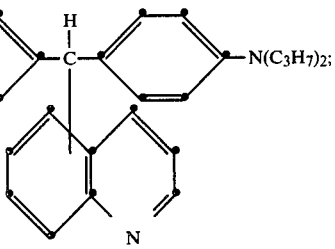

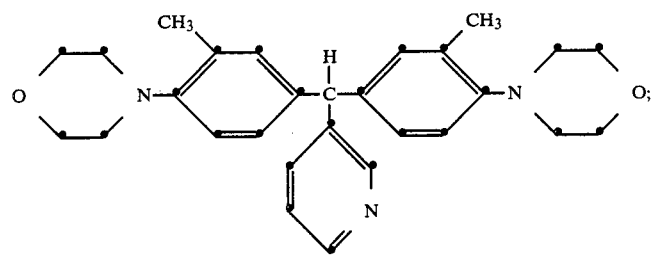

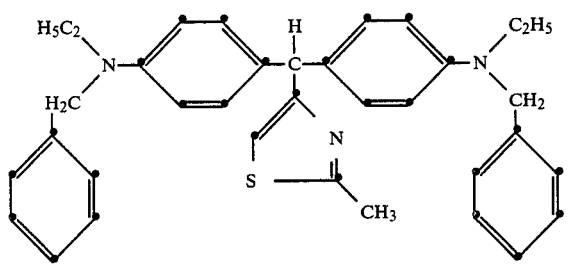

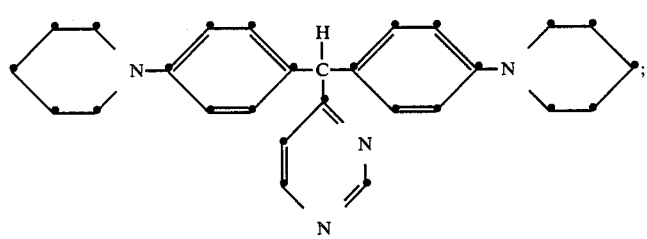

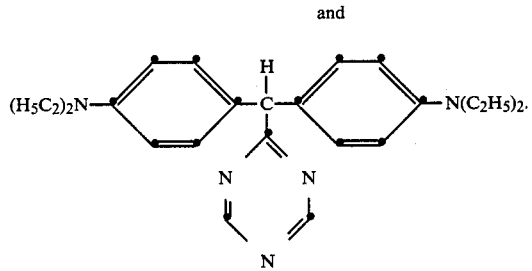

and

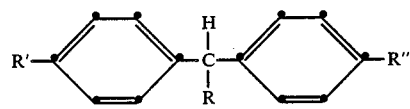

9. The composition of claim 8 wherein said leuco dye is compound I or II.

10. A composition for the determination of an analyte in an aqueous liquid, said composition comprising: (1) an interactive composition which produces hydrogen peroxide upon interaction with said analyte, (2) a substance having peroxidative activity and (3) a triarylmethane leuco dye which provides a dye having a maximum absorption at a wavelength equal to or greater than about 600 nm upon interaction with hydrogen peroxide, said leuco dye having the structure:

wherein R is a 5- to 15-membereed aromatic heterocyclic moiety provided that said moiety does not have an —NH— group in the ring; and R' and R" are independently open chain or cyclic amines.

11. The composition of claim 10 wherein said leuco dye has the structure:

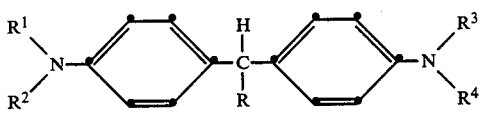

wherein $R^1$, $R^2$, $R^3$ and $R^4$ are independently alkyl, alkaryl, aralkyl, aryl or a heterocyclic moiety, or $R^1$ and $R^2$ or $R^3$ and $R^4$ independently taken together with the respective nitrogen atom, reperesent the atoms necessary to complete a heterocyclic ring.

12. A dry analytical element for the determination of hydrogen peroxide in an aqueous liquid, said element comprising: (1) a substance having peroxidative activity, and (2) a triarylmethane leuco dye which provides a dye having a maximum absorption at a wavelength equal to or greater than about 600 nm upon interaction with hydrogen peroxide, said leuco dye having the structure:

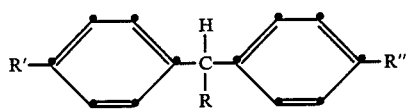

wherein R is a 5- to 15-membered aromatic heterocyclic moiety provided that said moiety does not have an —NH— group in the ring; and R' and R" are independently open chain or cyclic amines.

13. The element of claim 12 wherein said leuco dye has the structure:

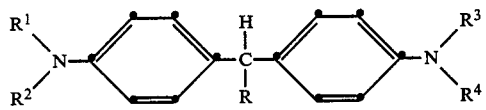

wherein $R^1$, $R^2$, $R^3$ and $R^4$ are independently alkyl, alkaryl, aralkyl, aryl or a heterocyclic moiety, or $R^1$ and $R^2$ or $R^3$ and $R^4$ independently taken together with the respective nitrogen atom, represent the atoms necessary to complete a heterocyclic ring.

14. The element of claim 12 comprising an interactive composition which produces hydrogen peroxide upon interaction with an analyte.

15. A dry analytical element for the determination of an analyte in an aqueous liquid, said element comprising:
a support having thereon a porous spreading zone and
(1) an interactive composition which produces hydrogen peroxide upon interaction with said analyte, (2) a substance having peroxidative activity and (3) a triarylmethane leuco dye which provides a dye having a maximum absorption at a wavelength equal to or greater than about 600 nm upon interaction with hydrogen peroxide, said leuco dye having the structure:

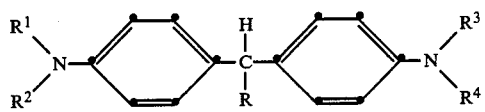

wherein R is a 5- to 15-membered aromatic heterocyclic moiety provided that said moiety does not have an —NH— group in the ring; and $R^1$, $R^2$, $R^3$ and $R^4$ are independently alkyl, alkaryl, aralkyl, aryl or a heterocyclic moiety, or $R^1$ and $R^2$ or $R^3$ and $R^4$ independently taken together with the respective nitrogen atom reperesent the atoms necessary to complete a heterocyclic ring.

16. The element of claim 15 wherein $R^1=R^3$ and $R^2=R^4$.

17. The element of claim 15 wherein said substance having peroxidative activity is peroxidase.

18. The element of claim 15 wherein $R^1$, $R^2$, $R^3$ and $R^4$ are the same.

19. The element of claim 18 wherein each of $R^1$, $R^2$, $R^3$ and $R^4$ is a lower alkyl of 1 to 6 carbon atoms.

20. The element of claim 15 wherein said leuco dye is selected from the group consisting of:

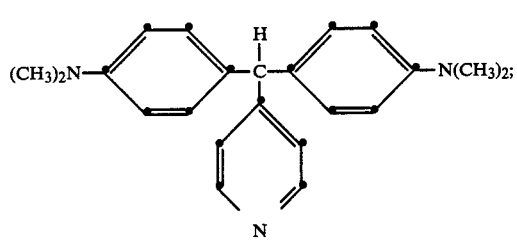

I.

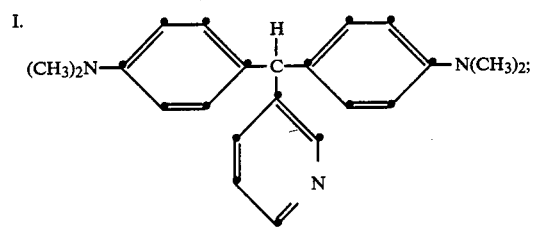

II.

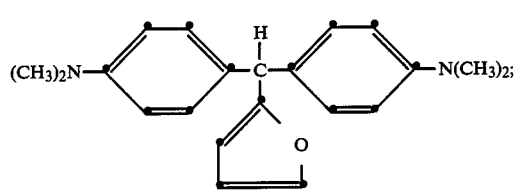

III.

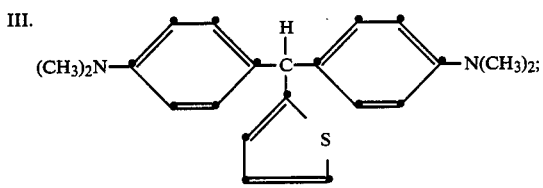

IV.

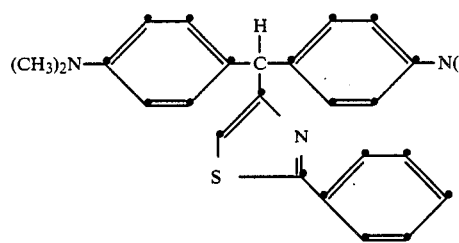 V.
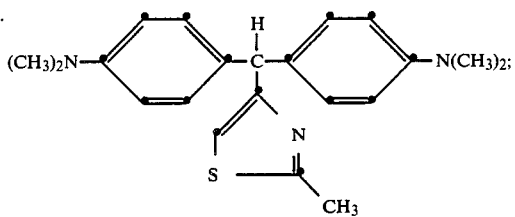 VI.
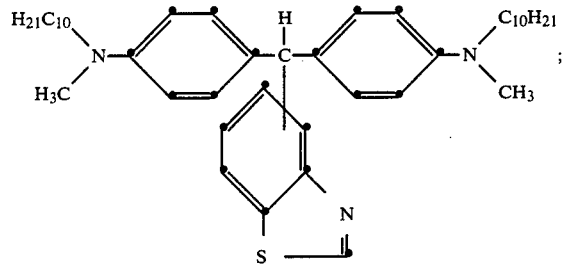 VII.
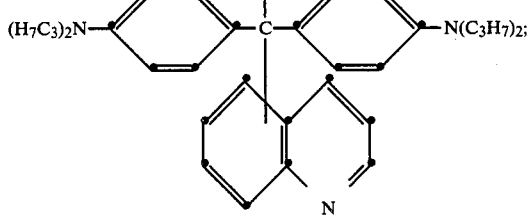 VIII.
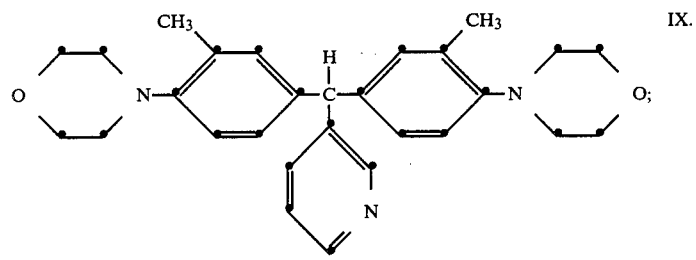 IX.
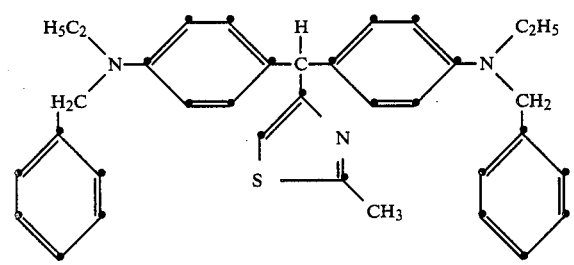 X.
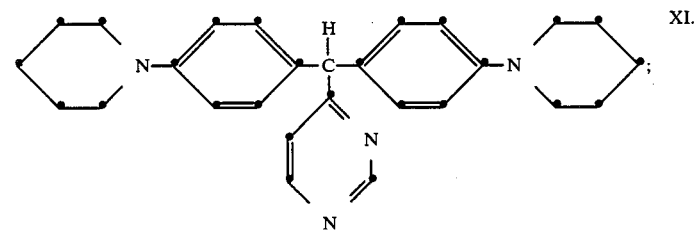 XI.
and
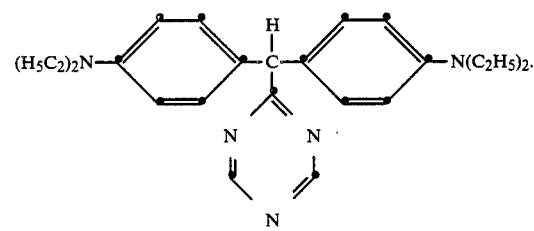 XII.

21. The element of claim 20 wherein said leuco dye is compound I or II.

22. A method for determing hydrogen peroxide or an analyte which reacts to produce hydrogen peroxide in an aqueous liquid, said method comprising the steps of:
A. physically contacting a sample of said liquid with a composition comprising a substance having peroxidative activity and tariarylmethane leuco dye which provides a dye having a maximum absorption at a wavelength equal to or greater than about 600 nm upon interaction with hydrogen peroxide, said leuco dye having the sructure:

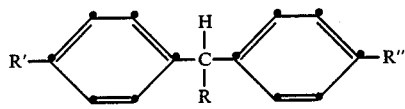

wherein R is a 5- to 15-membered aromatic heterocyclic moiety provided that said moiety does not have an —NH— group in the ring; and R' and R" are independently open chain or cyclic amines; and B. detecting said dye at a wavelength equal to or greater than about 600 nm.

23. The method of claim 22 wherein said leuco dye has the structure:

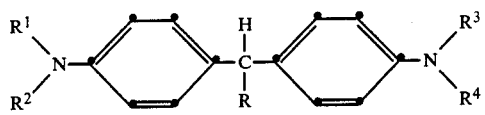

wherein $R^1$, $R^2$, $R^3$ and $R^4$ are independently alkyl, alkaryl, aralkyl, aryl or a heterocyclic moiety, or $R^1$ and $R^2$ or $R^3$ and $R^4$ independently taken together with the respective nitrogen atom, represent the atoms necessary to complete a heterocyclic ring.

24. The method of claim 22 wherein said leuco dye is in a dry analytical element.

25. The method of claim 22 wherein said contacting step a occurs in the presence of an interactive composition which reacts with said analyte to provide hydrogen peroxide.

* * * * *

UNITED STATES PATENT AND TRADEMARK OFFICE
CERTIFICATE OF CORRECTION

PATENT NO. : 4,670,385
DATED : June 2, 1987
INVENTOR(S) : Bruce E. Babb and Daniel S. Daniel It is certified that error appears in the above—identified patent and that said Letters Patent is hereby corrected as shown below:

Column 15, line 61, delete "$5 \times 10^{-2} 10^{-2} M$" and insert therefor --$5 \times 10^{-2} M$--.

Column 18, line 20, delete "complet" and insert therefor --complete--; same line, delete "ring," and insert therefor --ring.--; line 24, delete "heterocycliic" and insert therefor --heterocyclic--; lines 31-end, correct the formulas as follows:

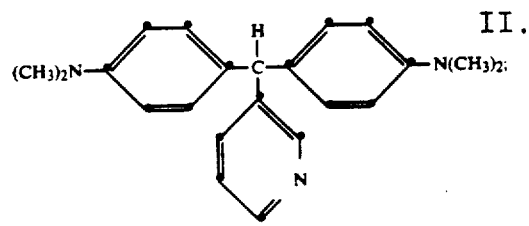

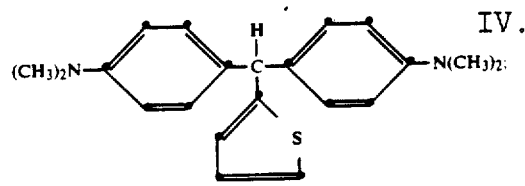

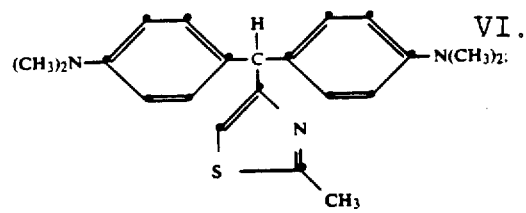

UNITED STATES PATENT AND TRADEMARK OFFICE
CERTIFICATE OF CORRECTION

PATENT NO. : 4,670,385
DATED : June 2, 1987
INVENTOR(S) : Bruce E. Babb and Daniel S. Daniel It is certified that error appears in the above-identified patent and that said Letters Patent are hereby corrected as shown below:

Column 19, line 68, delete "peroxide,said" and insert therefor --peroxide, said--.
Column 22, lines 44-end, correct the formulas as follows:

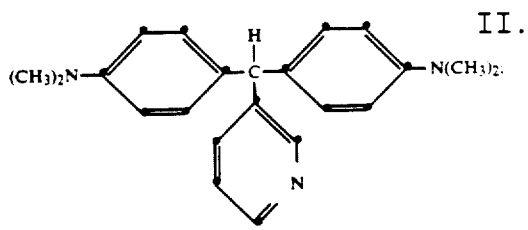

II.

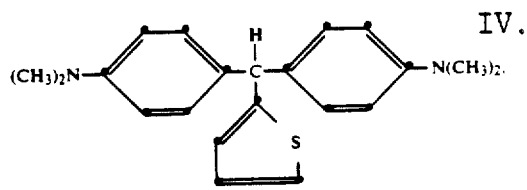

IV.

UNITED STATES PATENT AND TRADEMARK OFFICE
CERTIFICATE OF CORRECTION

PATENT NO. : 4,670,385

DATED : June 2, 1987

INVENTOR(S) : Bruce E. Babb and Daniel S. Daniel

It is certified that error appears in the above-identified patent and that said Letters Patent is hereby corrected as shown below:

Column 25, line 8, delete "tariarylmethane" and insert therefor -- triarylmethane --.

Signed and Sealed this

Twenty-seventh Day of October, 1987

Attest:

DONALD J. QUIGG

*Attesting Officer*

*Commissioner of Patents and Trademarks*